United States Patent [19]

Rewcastle et al.

[11] Patent Number: 4,479,000

[45] Date of Patent: Oct. 23, 1984

[54] CERTAIN ACRIDINYL-PHOSPHORAMIDATE COMPOUNDS

[75] Inventors: Gordon W. Rewcastle; Graham J. Atwell; Bruce C. Baguley; William A. Denny, all of Auckland, New Zealand

[73] Assignee: Development Finance Corporation of New Zealand, Wellington, New Zealand

[21] Appl. No.: 409,594

[22] Filed: Aug. 19, 1982

[30] Foreign Application Priority Data

Aug. 21, 1981 [NZ] New Zealand .................. 198115

[51] Int. Cl.³ .................. C07D 487/00; A01N 43/42
[52] U.S. Cl. ...................... 546/23; 424/200
[58] Field of Search ............... 546/23; 424/200

[56] References Cited

U.S. PATENT DOCUMENTS 4,258,191 3/1981 Dubicki et al. .................... 546/106

OTHER PUBLICATIONS

Chemical Abstracts, vol. 72, No. 7, Feb. 16, 1970, p. 318, Abstract No. 31645e—Columbus, Ohio & JP-A-69 27 388, (Taisho Pharmaceutical Co., Ltd.), (Nov. 13, 1969).
Journal of Chemical Society (C), vol. 21, 1971, pp. 3614–3617, R. S. Edmundson, "Phosphorylation of Diamines".

Primary Examiner—Alan L. Rotman
Attorney, Agent, or Firm—Brumbaugh, Graves, Donohue & Raymond

[57] ABSTRACT

The novel class of compounds of the present invention represented by the general formula (I):

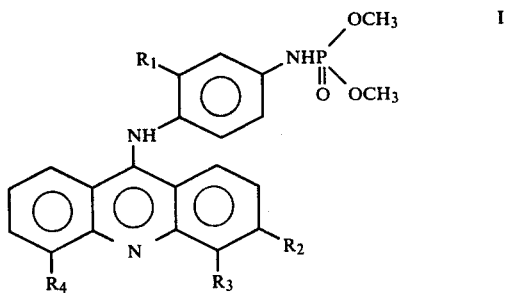

in which
$R_1$ represents H or $OCH_3$,
$R_2$ represents H, $OCH_3$, $CH_3$, halogen, $NO_2$, $NH_2$, $NHCOCH_3$ or $NHCOOCH_3$, and
$R_3$ and $R_4$ individually represent H, $CH_3$, $OCH_3$ or $CONHCH_3$, and the acid addition salts thereof, have unexpectedly high potency and activity in in vivo antitumour tests. The compounds are also bacteriostatic, and show toxicity towards mouse, hamster and human tumour cell lines in culture.

18 Claims, No Drawings

CERTAIN ACRIDINYL-PHOSPHORAMIDATE COMPOUNDS

BACKGROUND TO THE INVENTION

A number of derivatives of acridine have recently been studied for antitumour activity. In earlier work with the 9-anilinoacridines the marked antitumour effect of the 1'-methanesulphonamide derivative 4'-(9-acridinylamino)methanesulphonanilide or AMSA (compound 17, Table II herein) was revealed (G. J. Atwell, B. F. Cain and R. N. Seelye, *J.Med. Chem.*, 15, 611–615 (1972). A search for more dose-potent congeners culminated in the development of the clinical agent 4'-(9-acridinylamino)methanesulphon-m-anisidide, m-AMSA or amsacrine (compound 18 in Table II herein). (See the following articles: B. F. Cain and G. J. Atwell, *Europ. J.Cancer* 10, 539–549 (1974); B. F. Cain, G. J. Atwell and W. A. Denny, *J.Med.Chem.*, 18, 1110–1117 (1975); B. F. Cain, W. R. Wilson and B. C. Baguley, *Molecular Pharmacology*, 12, 1027–1035 (1976); B. F. Cain, G. J. Atwell and W. A. Denny, *J.Med.Chem.*, 19, 772–777 (1976); B. F. Cain and G. J. Atwell, *J.Med.-Chem.*, 19, 1409–1416 (1976); M. J. Waring, *Europ.J. Cancer*, 12, 995–1001 (1976); B. C. Baguley, W. R. Wilson, L. R. Ferguson and B. F. Cain, *Current Chemotherapy*, pp. 1210–1212 (1978); W. A. Denny, G. J. Atwell and B. F. Cain, *J.Med.Chem.*, 21, 5–10 (1978).)

The antitumour activity of a large range of AMSA and m-AMSA analogues containing variously substituted acridine nuclei has now been investigated, see for example G. J. Atwell, B. F. Cain and R. N. Seelye, *J.Med.Chem.*, 15, 611–615 (1972); B. F. Cain, R. N. Seelye and G. J. Atwell, *J.Med.Chem.*, 17, 922–930 (1974); B. F. Cain, G. J. Atwell and W. A. Denny, *J.Med.Chem.*, 18, 1110–1117 (1975), and *J.Med.Chem.*, 19, 772–777 (1976); B. F. Cain and G. J. Atwell, *J.Med.-Chem.*, 19, 1124–1129 and 1409–1416 (1976); G. J. Atwell, B. F. Cain and W. A. Denny, *J.Med.Chem.*, 20, 520–526, 987–996, 1128–1134, and 1242–1246 (1977); W. A. Denny, G. J. Atwell and B. F. Cain, *J.Med.Chem.*, 21, 5–10, (1978); W. A. Denny and B. F. Cain, *J.Med.-Chem.*, 21, 430–437 (1978); B. F. Cain, B. C. Baguley and W. A. Denny, *J.Med.Chem.*, 21, 658–668 (1978); L. R. Ferguson and W. A. Denny, *J.Med.Chem.*, 22, 251–255 (1979); W. A. Denny, G. J. Atwell and B. F. Cain, *J.Med.Chem.*, 22, 1453–1460 (1979); L. R. Ferguson and W. A. Denny, *J.Med.Chem.*, 23, 269–274 (1980); B. C. Baguley, W. A. Denny, G. J. Atwell and B. F. Cain, *J.Med.Chem.*, 24, 520–525 (1981); L. R. Ferguson and B. C. Baguley, *Mutation Research*, 82, 31–39 (1981); B. F. Cain, G. J. Atwell, B. C. Baguley and W. A. Denny, U.S. patent application Ser. No. 386,104, filed June 7, 1982 as a continuation-in-part of U.S. patent application Ser. No. 187,517 filed Sept. 15, 1980; and B. F. Cain and G. J. Atwell, U.S. patent application Ser. No. 257,857, filed Apr. 27, 1981 (now U.S. Pat. No. 4,366,318). During this work a number of derivatives containing different oxygen-containing substituents were evaluated at the 1'-position (e.g. NHCOCH$_3$, NHCOOCH$_3$, COOH) but these compounds were less active and/or less dose potent than those bearing the methanesulphonamide (B. C. Baguley, W. A. Denny, G. J. Atwell and B. F. Cain, *J.Med.-Chem.*, 24, 170–177 (1981).

SUMMARY OF THE INVENTION

We have now unexpectedly found that, of a number of phosphorus derivatives examined, a 1'-dimethylphosphoramidate group provides 9-anilinoacridine compounds of high potency and activity in in vivo antitumour tests. The compounds are also bacteriostatic, and show toxicity towards mouse, hamster and human tumour cell lines in culture.

It is the object of the present invention to provide dimethylphosphoramidates, in which the nitrogen atom is substituted by an acridinylaminophenyl group, having antibacterial and antitumour activity, processes for the preparation of these compounds, and the use of these compounds as antitumour agents.

DESCRIPTION OF THE INVENTION

The novel class of compounds of the present invention is represented by the general formula (I):

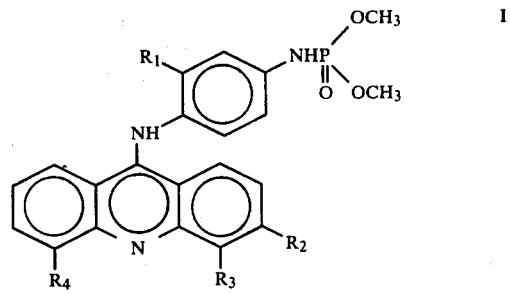

in which
$R_1$ represents H or OCH$_3$,
$R_2$ represents H, OCH$_3$, CH$_3$, halogen, NO$_2$, NH$_2$, NHCOCH$_3$ or NHCOOCH$_3$, and
$R_3$ and $R_4$ individually represent H, CH$_3$, OCH$_3$ or CONHCH$_3$
and the acid addition salts thereof.

A preferred class of compounds of the above formula (I) is that in which $R_1$ represents H or OCH$_3$, $R_2$ represents H, CH$_3$ or halogen, $R_3$ represents H, CH$_3$ or OCH$_3$ and $R_4$ represents H, CH$_3$ or CONHCH$_3$.

In another class of compounds of the above formula (I), $R_1$ represents H or OCH$_3$, $R_2$ represents H, OCH$_3$, CH$_3$, Cl, Br, I, NHCOCH$_3$ or NHCOOCH$_3$, $R_3$ represents H, CH$_3$ or OCH$_3$ and $R_4$ represents H.

The compounds of formula (I) form pharmaceutically acceptable salts with both organic and inorganic acids. Examples of suitable acids for salt formation are hydrochloric, hydrobromic, sulfuric, phosphoric, acetic, citric, oxalic, malonic, salicyclic, lactic, malic, fumaric, succinic, ascorbic, maleic, methanesulfonic, D-gluconic, 2-hydroxyethanesulphonic (i.e. isethionic), and the like acids.

The formation of the organophosphorus anilinoacridines of formula (I) involves mild acid-catalysed coupling of an appropriate 9-substituted acridine derivative with either dimethyl N-(4-aminophenyl)phosphoramidate or dimethyl N-(4-amino-3-methoxyphenyl)phosphoramidate in anhydrous solvents.

Accordingly, the compounds of formula (I), and acid addition salts thereof, are prepared by a process which comprises the coupling of a substituted acridine of the general formula (II):

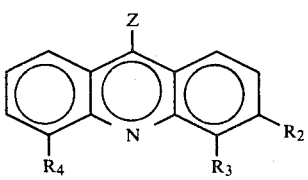

II wherein $R_2$, $R_3$ and $R_4$ are as defined above, and Z represents any suitable leaving group (e.g. methoxy, phenoxy, alkylthio or halogen but preferably chloro), with a dimethylphosphoramidate of the general formula (III):

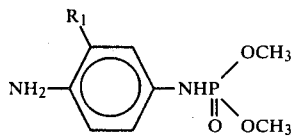

III wherein $R_1$ is defined as above, in an anhydrous solvent and in the presence of an acid, and, if desired, converting an acid addition salt of a compound of formula (I) into a free base compound of formula (I) and/or converting a compound of formula (I) into an acid addition salt thereof.

The acid-catalysed coupling reaction of compound (II) with compound (III) is performed in an anhydrous solvent, for example methanol, ethanol, 2-ethoxyethanol or N-methylpyrrolidone, with methanol being the preferred solvent. The reaction is preferably performed at temperatures between 30° C. and 100° C.

The acid addition salts are prepared by contacting the free base form with an equivalent amount of the desired acid in the conventional manner. The free base forms may be regenerated by treating the salt form with a base. For example, dilute aqueous base solutions may be utilized. Dilute aqueous potassium carbonate, ammonia, and sodium bicarbonate solutions are suitable for this purpose. The free base forms differ from their respective salt forms somewhat in certain physical properties such as solubility in polar solvents, but the salts are otherwise equivalent to their respective free base forms for purposes of the invention.

The intermediate compounds of formula (III) wherein $R_1$ represents H or $OCH_3$, i.e. dimethyl N-(4-aminophenyl)-phosphoramidate and dimethyl N-(4-amino-3-methoxyphenyl)-phosphoramidate, are novel compounds and form part of the present invention.

The dimethylphosphoramidates of formula (III) may be prepared by the method of Scheme I in which $R_1$ represents H and X represents $-NO_2$ or $PhCH_2OCONH-$ or $R_1$ represents $OCH_3$ and X represents $PhCH_2OCONH-$, and this general process also forms part of the present invention.

Scheme I

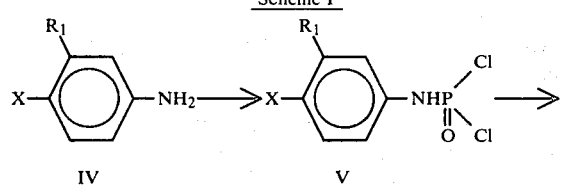

-continued
Scheme I

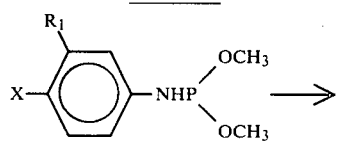

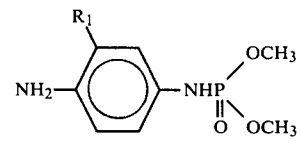

III

For the preparation of dimethyl N-(4-aminophenyl)-phosphoramidate (III; $R_1=H$), p-nitroaniline or benzyl N-(4-aminophenyl)carbamate is treated with $POCl_3$ to provide the dichloride (V; X=$NO_2$ or $PhCH_2OCONH$, $R_1=H$). (A. Michaelis, Annalen 326 223 (1903)). Treatment with sodium methoxide followed by reduction ($H_2/Pd/C$) yields the desired product, which can be isolated or used directly for coupling with a 9-substituted acridine.

Dimethyl N-(4-amino-3-methoxyphenyl)phosphoramidate (III; $R_1=OCH_3$) is elaborated from commercially available 2-methoxy-4-nitroaniline. Reaction with benzyl chloroformate followed by reduction of the nitro group (Fe, HCl) gives benzyl N-(4-amino-2-methoxyphenyl)carbamate (IV; X=$PhCH_2OCONH$, $R_1=OCH_3$). Treatment with $POCl_3$ followed by sodium methoxide yields (VI; X=$PhCH_2OCONH$, $R_1=OCH_3$). Hydrogenolysis ($H_2/Pd/C$) then provides the desired compound (III; $R_1=OCH_3$) which may be isolated or used directly for coupling with a 9-substituted acridine.

An alternative method for the preparation of dimethyl N-(4-amino-3-methoxyphenyl)phosphoramidate (III; $R_1=OCH_3$) is by direct reaction of benzyl N-(4-amino-2-methoxyphenyl)carbamate (IV; X=$PhCH_2OCONH$, $R_1=OCH_3$) with dimethyl phosphorobromidate or dimethylphosphorochloridate to give (VI; X=$PhCH_2OCONH$, $R_1=OCH_3$), which is treated as above to provide the desired compound (III; $R_1=OCH_3$).

The 9-chloroacridines of formula (II; Z=Cl) may be prepared using published methods (e.g. B. F. Cain, G. J. Atwell and W. A. Denny, J.Med.Chem. 18, 1110–1117 (1975) to produce the appropriately substituted 9-chloroacridine derivatives. The following novel procedure (Scheme II) in which Y represents halogen can be used for obtaining derivatives of general formula (II) where Z represents Cl, $R_2$ represents halogen, $R_3$ represents H and $R_4$ represents $CONHCH_3$:

Scheme II

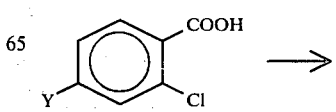

-continued
Scheme II

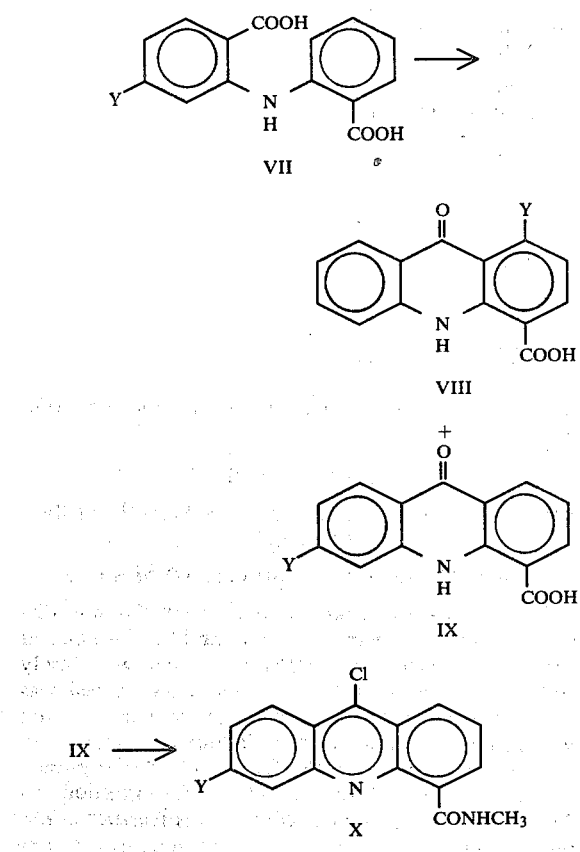

Reaction of a 2-chloro-4-halobenzoic acid with anthranilic acid in the presence of copper and an acid acceptor (preferably potassium carbonate) gives an essentially quantitative yield of the diacid (VII). Ring closure with mineral acid reagents gives an approximately 1:2 mixture of the carboxyacridanones (VIII) and (IX), which can be conveniently separated by fractional crystallization of the potassium salts from aqueous EtOH. After removal of the less soluble 1-halo-4-carboxyacridanone potassium salt, the more soluble 3-halo-5-carboxyacridanone potassium salt is obtained by concentration of the mother liquors.

Crystallization of the liberated acid from DMF (in which the 3-halo-5-carboxyacridanone is the less soluble isomer) affords pure product. Activation with $SOCl_2$ or $POCl_3$ and reaction with aqueous $CH_3NH_2$ provides the desired 9-chloroacridine. The intermediate compounds of the general formula (IX) in Reaction Scheme II, are novel compounds.

The 9-bromoacridines of formula (II; Z=Br) can be prepared from either the appropriate diphenylamine-2-carboxylic acids by treatment with phosphoryl bromide, or from the acridone by reaction with thionyl bromide. 9-Phenoxy- and 9-methoxy-acridines can be prepared by the methods given in Albert, "The Acridines" Second Edition, Edward Arnold Ltd., London (1966). 9-Alkylthio heterocycles, and the precursor 9-acridanthiones can be prepared by the methods cited in E. F. Elslager et al, *J.Med.Chem.* 14, 782–788 (1971).

The coupling of the 9-chloroacridine of formula (II; Z-Cl) with the phosphoramidate of formula (III) may be performed according to the following procedure which is given by way of illustration of the process of the invention.

A methanolic solution of 1.1 equivalents of the phosphoramidate compound (preferably obtained in situ by hydrogenation of the nitro or benzylurethane precursor over palladium on charcoal) is combined with 1 equivalent of the appropriate 9-chloroacridine derivative dissolved or suspended in methanol, and one or two drops of concentrated hydrochloric acid are added to initiate the reaction (as evidenced by the appearance of a deep red colouration). At the completion of the coupling reaction (5–10 minutes at room temperature in the case of 9-chloroacridine and up to 15 minutes at reflux in the case of much less soluble 4-methyl derivative) the solution is concentrated to a small volume under vacuum, and allowed to stand as crystallization commences. After being diluted with ethyl acetate to ensure complete crystallization, the mixture is filtered and the dark-red hydrochloride salt washed with dry acetone. The product can be purified by recrystallization from methanol-ethyl acetate.

Conversion of the hydrochloride salt to the free base can be achieved by the addition of 1.1 equivalents of aqueous $KHCO_3$ to an aqueous methanolic solution of the salt. Removal of the methanol gives the free base which can be recrystallized from either aqueous methanol or anhydrous solvents such as ethyl acetate or benzene. Alternatively, the free bases can be isolated by a procedure that eliminates the need to firstly isolate them as the hydrochloride salts. After completion of the initial coupling reaction a slight excess of aqueous $KHCO_3$ is added to the methanolic solution, and the solvent is removed under vacuum. After being extracted into ethyl acetate and washed with water, the product is extracted into aqueous methanesulphonic acid thereby leaving any acridone impurities in the organic layer. After neutralization of the aqueous layer with $KHCO_3$ the product is again extracted into ethyl acetate, and the solution dried over $Na_2SO_4$, and the solvent removed under vacuum to give the free base which can be recrystallized as described earlier.

Other acid addition salts (e.g. methanesulphonate) can be formed by treating the free base in methanol with an equivalent of the appropriate acid. Isolation of the product salt is achieved by dilution of the solution with ethyl acetate.

The following Table I sets out physicochemical and biological data for 16 compounds within the general formula (I) and preparable by the process of the invention. In Table I the following terms and abbreviations are used:

Anion = the anionic component of the acid addition salt of the compound of formula (I). Compounds prepared as the free base form of formula (I) are shown as (base). These compounds are converted to acid addition salts (normally by addition of the appropriate concentration of isethionic acid) before use in in vivo biological tests.

MW = molecular weight.

MP = melting point in °C. Decomposition of the sample is shown by the abbreviation dec.

Rm = a measure of the compound's lipophilic-hydrophilic balance from reversed-phase partition chromatography. Rm is linearly related to partition coefficients obtained in the 1-octanol/water system.

$R_1$, $R_2$, $R_3$ and $R_4$ refer to formula (I).

TABLE I

| Compound No. | $R_1$ | $R_2,R_3,R_4$ | Anion | Formula | Mp °C. | MW | Rm |
|---|---|---|---|---|---|---|---|
| 1 | H | H | $CH_3SO_3$ | $C_{21}H_{20}N_3O_3P \cdot CH_3SO_3H$ | 230(dec) | 489.5 | 0.31 |
| 2 | $OCH_3$ | H | (base) | $C_{22}H_{22}N_3O_4P$ | 135(dec) | 423.4 | 0.47 |
| 3 | H | 3-$CH_3$ | $Cl^-$ | $C_{22}H_{22}N_3O_3P \cdot HCl$ | 250(dec) | 443.5 | 0.49 |
| 4 | H | 3-Cl | $Cl^-$ | $C_{21}H_{19}ClN_3O_3P \cdot HCl$ | >350 | 464.0 | 0.46 |
| 5 | $OCH_3$ | 3-Cl | $Cl^-$ | $C_{22}H_{21}ClN_3O_4P \cdot HCl$ | 205(dec) | 494.0 | 0.61 |
| 6 | H | 3-Br | $Cl^-$ | $C_{21}H_{19}BrN_3O_3P \cdot HCl$ | 305(dec) | 508.7 | 0.47 |
| 7 | $OCH_3$ | 3-Br | $Cl^-$ | $C_{22}H_{21}BrN_3O_4P \cdot HCl$ | 212(dec) | 538.7 | 0.57 |
| 8 | H | 3-$NO_2$ | (base) | $C_{21}H_{19}N_4O_5P$ | 219(dec) | 438.4 | 0.14 |
| 9 | H | 4-$OCH_3$ | $Cl^-$ | $C_{22}H_{22}N_3O_4P \cdot HCl$ | 242(dec) | 459.9 | 0.33 |
| 10 | $OCH_3$ | 4-$OCH_3$ | (base) | $C_{23}H_{24}N_3O_5P$ | 178 | 453.4 | 0.47 |
| 11 | H | 4-$CONHCH_3$ | $Cl^-$ | $C_{23}H_{23}N_4O_4P \cdot HCl$ | 235(dec) | 486.9 | 0.18 |
| 12 | $OCH_3$ | 4-$CONHCH_3$ | $Cl^-$ | $C_{24}H_{25}N_4O_5P \cdot HCl$ | 223(dec) | 516.9 | 0.28 |
| 13 | H | 4-$CH_3$ | (base) | $C_{22}H_{22}N_3O_3P$ | 225 | 407.4 | 0.46 |
| 14 | $OCH_3$ | 4-$CH_3$ | (base) | $C_{23}H_{24}N_3O_4P$ | 183 | 437.4 | 0.44 |
| 15 | $OCH_3$ | 3-Cl,5-$CONHCH_3$ | $Cl^-$ | $C_{24}H_{24}ClN_4O_5P \cdot HCl$ | 244(dec) | 551.4 | 0.54 |
| 16 | H | 4,5-di$CH_3$ | $Cl^-$ | $C_{23}H_{24}N_3O_3P \cdot HCl$ | 205(dec) | 457.9 | 0.37 |

The following Examples A, B and C illustrate the preparation of compounds of the general formula (I).

EXAMPLE A

Preparation of Compound 1 of Table I (via the method of Scheme I)

N-(4-Nitrophenyl)phosphoramidoyl Dichloride (V; X=$NO_2$, $R_1$=H)

75 g (0.51 mol) of 4-nitroaniline and 150 ml distilled $POCl_3$ were mixed together in a 500 ml flatbottomed flask equipped with a reflux condenser and a calcium chloride drying tube. The mixture was heated to reflux (oil bath) and maintained at that temperature until HCl evolution ceased (2-3 hours). The homogeneous solution was allowed to cool and the product crystallized out on standing overnight at 5° C. After being filtered off the product was washed with petroleum ether and dried in vacuo to yield 130 g (94%) of the dichloride.

Dimethyl N-(4-Nitrophenyl)phosphoramidate (VI; X=$NO_2$, $R_1$=H)

38.1 g (0.15 mol) of the crude N-(4-nitrophenyl)phosphoramidoyl dichloride was added in portions with stirring to a cooled solution of 11.4 g (0.5 mol, 3.3 equivalents) of sodium in 150 ml dry methanol. After being stirred for a further 5 minutes at low temperature the mixture was diluted with 750 ml of ice cold water and filtered. Treatment of the filtrate with dilute hydrochloric acid gave a precipitate of the diester which was collected, washed several times with water, and dried in vacuo. Yield 33.4 g (90.5%) m.p. 163°-164° C., after recrystallization from aqueous methanol.

Dimethyl N-(4-aminophenyl)phosphoramidate (III; $R_1$=H)

The above nitrocompound (10 g, 0.04 mol) was hydrogenated over Pd/C in EtOH for 15 min. The solution was filtered, concentrated to small volume and the product precipitated with petroleum ether. Yield 8 g (93%), m.p. 125° C. after crystallization from ethyl acetate.

Compound 1 of Table I

A solution of the above amine (1.0 g, 4.7 mM) in methanol was added to a suspension of 9-chloroacridine (0.90 g, 4.2 mM) in methanol. A drop of cHCl was added and the mixture was warmed until all solids dissolved. The solution was then concentrated to small volume (20 mL) under vacuum, and ethyl acetate was added to complete crystallization of the hydrochloride salt.

EXAMPLE B

Preparation of Compound 14 of Table I (via the method of Scheme I)

Benzyl N-(2-methoxy-4-nitrophenyl)carbamate

2-Methoxy-4-nitroaniline, 51 g (0.3 mol), was dissolved in 135 ml of acetone containing 12 g of MgO, and 65 ml of commercial benzylchloroformate was slowly added to the stirred mixture. After 4 hours the flask was warmed to redissolve the precipitate and the mixture was stirred overnight. DMF (100 ml) was added, and the mixture was heated to dissolve all of the product before being filtered through celite. After dilution with 250 ml of ethanol the hot solution was further diluted with water until almost cloudy, and allowed to cool. The pale yellow crystals were collected, washed well with 50% aqueous ethanol, and dried. Yield 86.0 g, 94%, m.p. 130°-131° C.

Benzyl N-(4-amino-2-methoxyphenyl)carbamate (IV; X=$PhCH_2OCONH$, $R_1$=$OCH_3$)

The benzyl N-(2-methoxy-4-nitrophenyl)carbamate, 50 g (0.18 mol), was dissolved in a hot mixture of 200 ml DMF, 100 ml $H_2O$ and 15 ml concentrated HCl, and the stirred solution was treated slowly with 75 g Fe powder at a rate so as to maintain gentle reflux. When the reaction was complete (15-30 minutes), concentrated $NH_3$(aq) was added to precipitate Fe salts, the mixture was diluted with 250 ml EtOH and filtered through celite. After removal of the solvent under vacuum the residue was extracted with aqueous methanesulphonic acid and the solution was clarified with charcoal-celite. Neutralization with $NH_3$ (aq) gave the aminocarbamate which was collected, washed well with water, and dried. Yield 43.8 g, 97%, m.p. 77°-78° C. (toluene-petroleum ether).

N-(4-Benzyloxycarbonylamino-3-methoxyphenyl)phosphoramidoyl Dichloride (V; X=$PhCH_2COCONH$, $R_1$=$OCH_3$)

A solution of benzyl N-(4-amino-2-methoxyphenyl)-carbamate (IV; X=$PhCH_2OCONH$, $R_1$=$OCH_3$) (20 g, 73.5 mM) in $CH_2Cl_2$ (25 mL) was added over 5 min to a stirred, icecold, mixture of dry pyridine (25 mL) and $POCl_3$ (100 mL), and the resulting mixture was stirred below 5° C. for a further 2 h. Precipitation with petroleum ether (500 mL) at −10° C. for 15 h gave crude solid product, which was isolated by decantation and washed with two portions of petroleum ether.

Dimethyl N-(4-benzyloxycarbonylamino-3-methoxyphenyl)phosphoramidate (V1; X=PhCH$_2$OCONH, R$_1$=OCH$_3$)

The above crude product (29 g) was added slowly to a cooled solution of Na (8.5 g, 5 equivalent) in CH$_3$OH (250 mL). After 5 mins the solution was neutralized with acetic acid, and the solvent removed under vacuum. The residue was extracted into ethyl acetate, washed successively with dilute HCl, water, KHCO$_3$ solution, and brine, and dried over MgSO$_4$. Removal of the solvent gave an oil which was triturated with a small amount of ethyl acetate to give 4.5 g (16%) of dimethyl N-(4-benzyloxycarbonylamino-3-methoxyphenyl)phosphoramidate, m.p. 115° C. (acetone-petroleum ether). Chromatography of the mother liquors yielded an additional 20% of crystalline compound.

Dimethyl N-(4-amino-3-methoxyphenyl)phosphoramidate (III; R$_1$=OCH$_3$)

Hydrogenolysis of the above carbamate (5 g, 13 mM) in EtOH over Pd/C for 1 h gave the aminocompound upon filtration, concentration and precipitation with petroleum ether. Yield 3.0 g (95%), m.p. 122°-123° C. after crystallization from ethyl acetate.

4-Methyl-9-chloroacridine (II; Z=Cl, R$_2$ and R$_4$=H, R$_3$=CH$_3$)

A heterogeneous mixture of o-chlorobenzoic acid (3.12 g, 0.02 mol), o-toluidine (3.21 g, 0.03 mol), anhydrous K$_2$CO$_3$ (3.45 g, 0.025 mol), Cu powder (0.05 g), CuCl$_2$ (0.05 g) and 2-ethoxyethanol (10 ml) was stirred and heated under reflux conditions in an oil bath at 105° for 3 hours. After cooling the mixture was acidified with excess concentrated HCl and diluted with water. The resulting solid was washed well with water, dissolved in an excess of aqueous Na$_2$CO$_3$ by boiling, stirred with a generous quantity of decolourizing charcoal and then filtered through a Celite pad. Slow addition of dilute aqueous acetic acid to the hot stirred solution first initiated separation of a quantity of black impurity which was filtered off and addition of excess aqueous HCl then precipitated the product, N-(2-methylphenyl)anthranilic acid. One crystallization from acetone-methanol-water (by concentration of a boiling solution) provided material of acceptable purity (65% yield). The product may be recrystallized from benzene to provide TLC homogeneous product, m.p. 193°-194° C. (lit m.p. 190°-191° C.).

The N-(2-methylphenyl)anthranilic acid (5.0 g) and POCl$_3$ (15 ml) were heated together under reflux conditions for 1 hour and then concentrated in vacuo on the steam bath to remove most of the excess POCl$_3$. The resulting oily residue was cooled, dissolved in chloroform and then poured with stirring into an ice-excess NH$_4$OH mix. The chloroform layer was washed with dilute aqueous NH$_4$OH, water, dried boiling dry ligroine (bp 95°-115°) or with a large volume of petroleum ether and the filtered solution was evaporated to dryness providing the product in 82% yield, sufficiently pure for use in the next stage (lit. m.p. 94° C.).

Compound 14 of Table I

A solution of the dimethyl N-(4-amino-3-methoxyphenyl)phosphoramidate (1.5 g, 6.2 mM) in methanol was added to a suspension of 4-methyl-9-chloroacridine (1.5 g, 6.06 mM) in methanol and the mixture was gently refluxed with 1 drop of cHCl until all the solids had dissolved (about 15 min). The solution was then concentrated to small volume (20 mL) and ethyl acetate was added to complete precipitation of the hydrochloride salt which was then converted to the free base.

EXAMPLE C

Preparation of Compound 15 of Table I

Alternative Preparation of dimethyl N-(4-amino-3-methoxyphenyl)phosphoramidate (III; R$_1$=OCH$_3$)

A solution of 15.5 ml Br$_2$ (0.3 mol) in 50 ml of petroleum ether was slowly added with stirring to a cooled solution of 30 ml trimethylphosphite (0.3 mol) in 100 ml of petroleum ether. At the completion of the addition (if necessary) trimethylphosphite was added dropwise to decolorize any excess bromine, and the upper layer was decanted off. Dissolved methyl bromide was removed under vacuum at room temperature and the remaining dimethyl phosphorobromidate was used without further purification.

Benzyl N-(4-amino-2-methoxyphenyl)carbamate (IV; X=PhCH$_2$OCONH, R$_1$=OCH$_3$) (10 g, 3.6 mmol), was dissolved in 50 ml of dry pyridine and an excess (1.5-2.0 equivalents) of freshly prepared dimethyl phorphorobromidate was slowly added at 0° C. with stirring. The resulting mixture was allowed to warm slowly to room temperature, and stirred overnight before being quenched with water and extracted with ethyl acetate. The organic layer was washed successively with dilute methanesulfonic acid, water, dilute KHCO$_3$ solution, brine, and dried over Na$_2$SO$_4$ and the solvent was removed under vacuum. The residue was chromatographed on silica (CH$_2$Cl$_2$—MeOH, 25:1) to give dimethyl N-(4-benzyloxycarbonylamino-3-methoxyphenyl)phosphoramidate (VI, X—PhCH$_2$OCONH, R$_1$=OCH$_3$) as an oil, which crystallized on trituration with acetone. Yield 5.68 g (41%), mp 115° C. (acetone-petroleum ether).

This was converted to the desired dimethyl N-(4-amino-3-methoxyphenyl)phosphoramidate (III; R$_1$=OCH$_3$) by the method given in Example B.

Preparation of methyl 3,9-dichloro-5-carboxamidoacridine (X,Y=Cl) by the method of Scheme II 2-(2'-carboxy-N-phenyl)-4-chloroanthranilic acid (VII; Y=Cl)

Anthranilic acid (38 g, 0.28M), 2,4-dichlorobenzoic acid (50 g, 0.26M) and potassium carbonate (57 g, 0.42M) were suspended in 2-ethoxyethanol (200 mL) and heated at 50° C. until gas evolution ceased. Copper/copper oxide (1:1 mixture, 0.4 g) was added, and the mixture stirred at 120° C. for 45 min. The cooled mixture was diluted with water, filtered through celite and acidified with 2N HCl. The precipitate was collected and washed well with water to yield the desired diacid, suitable for the next step. Yield 73 g, 96%.

3-Chloro-5-carboxyacridanone (IX; Y=Cl).

The above crude diacid (50 g) was dissolved in cH$_2$SO$_4$ (150 mL) and kept at 100° C. for 2 h. The cooled mixture was poured slowly into hot water, and the mixture was boiled briefly to coagulate the precipitate. The solid was collected and washed well with water to yield the mixed chlorocarboxyacridanones (VIII and IX; Y=Cl) 45 g, 96%.

This mixture (70 g) was suspended in boilding EtOH (1200 mL) and a hot solution of KOH (70 g) in water (1200 mL) was added rapidly. All solids dissolved, followed rapidly by precipitation of the potassium salt of 1-chloro-4-carboxyacridanone (VIII; Y=Cl). The suspension was allowed to cool to 30° C. and the solid was collected (62 g=53 g of free acid). The filtrate was concentrated to 1000 mL and kept at 20° C. for 24 h, when the K salt of the 3-chloro-5-carboxyacridanone (IX; Y=Cl) precipitated and was collected (12.5 g=10.3 g of free acid). Crystallization from DMF gave yellow microcrystals, m.p. 360° C.

Methyl 3,9-dichloro-5-carboxamidoacridine

3-Chloro-5-carboxyacridinone (2.0 g, 7.3 mM) was suspended in SOCl$_2$ (25 mL) and a drop of DMF, and refluxed gently for 1 h. Volatiles were evaporated under reduced pressure and the residue was azeotroped with dry benzene to removal all SOCl$_2$. The residue was dissolved in dry CH$_2$Cl$_2$ and poured onto icecold aqueous CH$_3$NH$_2$. The organic layer was washed with water and saturated NaCl and dried. Evaporation of solvent gave the desired chloroacridine (1.8 g, 84%).

Compound 15 of Table I

The above methyl 3,9-dichloro-5-carboxamidoacridine (1.5 g, 5.1 mM) and 5.2 mM of the dimethyl N-(4-amino-3-methoxyphenyl)phosphoramidate (III; R$_1$=OCH$_3$) were coupled conventionally in methanol to give the red hydrochloride salt of compound 15.

The compounds of general formula (I), and particularly the compounds listed in Table I, have antitumour activity in both in vitro and in vivo test systems, as shown by the data of Table II. Many of them are more dose potent than the corresponding methanesulphonamido analogues (Table II). The compounds also show broad-spectrum antibacterial activity. Specifically, compound 1 is active against the bacterial aerobacter aerogenes, alcaligenes viscolactics, eschereichia coli, bacillus subtilis, sarcina lutea, micrococcus lysodeikticus, neisseria catarrhalis, staphylococcus aureus, xanthomonas phaseoli and streptococcus faecalis.

The following Table II shows the activity of compounds of general formula (I) towards L1210 tumour cells in culture and the P388 leukaemia in mice.

The P388 mouse leukaemia system has been shown by studies at the National Cancer Institute, U.S.A., to be a useful system for detecting agents with antitumour activity against clinical cancer (A. Goldin, J. M. Venditti, J. S. MacDonald, F. M. Muggia, J. E. Henney and V. T. De Vita, Europ.J.Cancer 17, 129–142 (1981).

The following terms and abbreviations are used in Table II:

Tumour P388 i.p.—P388 cells were obtained as frozen stocks from Mason Research Inc., U.S.A., and passaged introperitoneally according to standard methods (Cancer Chemother.Rep. 3, Part 3, page 9 (1972) in DBA-2 mice of either sex. Groups of six F1 hybrid mice (DBA-2 male×C57 B1 female, g weight 20±1 g) were injected intraperitoneally with 10$^6$ cells on day 0.

O.D.=optimal drug dose (in milligrams per kilogram), administered as a solution in 0.1 ml of 30% v/v ethyl alcohol in water on days 1, 5 and 9 after tumour inoculation. The drug is administered as a soluble acid addition salt.

ILS=percentage increase in life span of treated animals over that of groups of control animals injected with tumour alone. The average survival of control mice was 11 days. Values of ILS greater than 20% are considered statistically significant.

ID$_{50}$=the nanomolar concentration of drug which when added to cultures of murine L1210 leukaemia cells over a period of 70 hours, reduces the resultant counted number of leukaemia cells by 50% (B. C. Baguley and R. Nash, Europ.J.Cancer 17, 671–679, 1981).

Y. implies a significant value of drug activity at the stated dose.

TABLE II

BIOLOGICAL DATA FOR THE COMPOUNDS OF TABLE I

| No. | L1210 culture data ID$_{50}$ | P388 in vivo data OD | ILS | Active |
|---|---|---|---|---|
| 1 | 15 | 33 | 74 | Y |
| 2 | 70 | 8.9 | 67 | Y |
| 3 | 6.8 | 30 | 80 | Y |
| 4 | 16 | 30 | 54 | Y |
| 5 | 12 | 13.3 | 78 | Y |
| 6 | 15 | 45 | 76 | Y |
| 7 | 4.9 | 13.3 | 83 | Y |
| 8 | 74 | 8.9 | 22 | Y |
| 9 | 20 | 20 | 44 | Y |
| 10 | 12 | 8.9 | 76 | Y |
| 11 | 97 | 45 | 38 | Y |
| 12 | 18 | 30 | 118 | Y |
| 13 | 8.9 | 20 | 111 | Y |
| 14 | 18 | 8.9 | 106 | Y |
| 15 | 50 | 45 | 79 | Y |
| 16 | 17 | 45 | 109 | Y |
| 17 AMSA for comparison | 35 | 150 | 93 | Y |
| 18 m-AMSA for comparison | 35 | 13.3 | 78 | Y |

It is clear from the data of Table II that the dimethylphosphoramidates of general formula (I) are active antitumour agents, giving significant levels of life extension when tested against the P388 leukaemia system when given by intraperitoneal injection. The compounds also show antitumour activity when given by oral and intravenous routes. They also show high cytotoxicity towards cultured L1210 leukaemia cells (Table II), and are active in a number of cultured tumour cell lines, including those originating from human colon and breast tumours.

These compounds are thus indicated for use as antitumour agents, and the present invention also provides pharmaceutical compositions having antitumour activity and comprising at least one compound of the general formula (I) or a pharmaceutically acceptable acid addition salt thereof, and one or more pharmaceutically acceptable carriers or diluents.

The present invention further provides a method for treating tumours in a patient which comprises administering to the patient an antitumour effective amount of a compound of the general formula (I) or a pharmaceutically acceptable acid addition salt thereof.

The active compounds may be orally administered, for example, with an inert diluent or with an assimilable edible carrier, or they may be enclosed in hard or soft shell gelatin capsules, or they may be compressed into tablets, or they may be incorporated directly with the food of the diet. For oral therapeutic administration, the active compounds may be incorporated with excipients and used in the form of ingestible tablets, buccal tablets, troches, capsules, elixirs, suspensions, syrups, wafers and the like. Such compositions and preparations should contain at least 0.1% of active compound. The percentage of the compositions and preparations may, of course, be varied and may conveniently be between about 2 and about 60% of the weight of the unit. The amount of active compound in such therapeutically useful compositions is such that a suitable dosage will be obtained. Preferred compositions or preparations according to the present invention are prepared so that an oral dosage unit form contains between about 5 and about 200 milligrams of active compound.

The tablets, troches, pills, capsules and the like may also contain the following: a binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavouring agent such as peppermint, oil of wintergreen or cherry flavouring. When the dosage unit form is a capsule, it may contain, in addition to materials of the above type, a liquid carrier. Various other materials may be present as coatings or to otherwise modify the physical form of the dosage unit. For instance, tablets, pills or capsules may be coated with shellac, sugar or both. A syrup or elixir may contain the active compound, sucrose as a sweetening agent, methyl and propylparabens as preservatives, a dye and flavouring such as cherry or orange flavour. Of course, any material used in preparing any dosage unit form should be pharmaceutically pure and substantially non-toxic in the amounts employed. In addition, the active compounds may be incorporated into sustained-release preparations and formulations.

The active compounds may also be administered parenterally or intraperitoneally. Solutions of the active compound as a free base or pharmaceutically acceptable salt can be prepared in water suitably mixed with a surfactant such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

It is especially advantageous to formulate parenteral compositions in dosage unit form for ease of administration and uniformity of dosage. "Dosage unit form" as used herein refers to physically discrete units suitable as unitary dosages for the mammalian subjects to be treated; each unit containing a predetermined quantity of active material calculated to produce the desired therapeutic effect in association with the required pharmaceutical carrier. The specifications for the novel dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired as herein disclosed.

The principal active ingredient is compounded for convenient and effective administration in effective amounts with a suitable pharmaceutically acceptable carrier in dosage unit form as hereinbefore disclosed. A unit dosage form can, for example, contain the principal active compound in amounts ranging from about 0.1 to about 400 mg, with from about one to about 30 mg being preferred. Expressed in proportions, the active compound is generally present in from about 0.1 to about 400 mg/ml of carrier. In the case of compositions containing supplementary active ingredients, the dosages are determined by reference to the usual dose and manner of administration of the said ingredients.

What is claimed is:

1. A compound represented by the general formula (I):

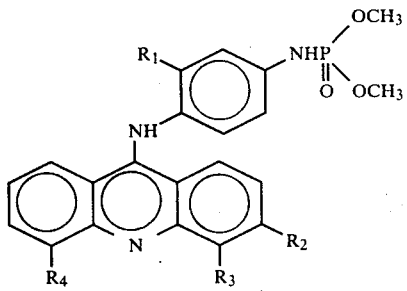

in which
 $R_1$ represents H or $OCH_3$,
 $R_2$ represents H, $OCH_3$, $CH_3$, Cl, Br, I, $NHCOCH_3$ or $NHCOOCH_3$,
 $R_3$ represents H, $CH_3$ or $OCH_3$ and
 $R_4$ represents H,
or a pharmaceutically acceptable acid addition salt thereof.

2. A compound represented by the general formula (I):

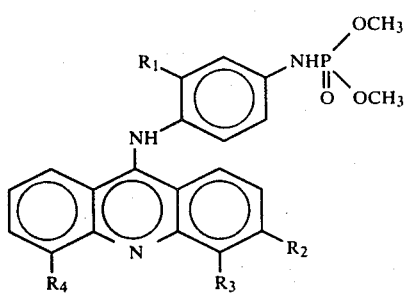

in which
 $R_1$ represents H or $OCH_3$,
 $R_2$ represents H, $CH_3$ or halogen,
 $R_3$ represents H, $CH_3$ or $OCH_3$ and
 $R_4$ represents H, $CH_3$ or $CONHCH_3$,
or a pharmaceutically acceptable acid addition salt thereof.

3. A compound according to claim 2 in which $R_1$ represents H, $R_2$ represents $CH_3$, and $R_3$ and $R_4$ each represent H.

4. A compound according to claim 2 in which $R_1$ represents H, $R_2$ represents Cl and $R_3$ and $R_4$ each represent H.

5. A compound according to claim 2 in which $R_1$ represents $OCH_3$, $R_2$ represents Cl and $R_3$ and $R_4$ each represent H.

6. A compound according to claim 2 in which $R_1$ represents H, $R_2$ represents Br and $R_3$ and $R_4$ each represent H.

7. A compound according to claim 2 in which $R_1$ represents $OCH_3$, $R_2$ represents Br and $R_3$ and $R_4$ each represent H.

8. A compound according to claim 2 in which $R_1$ represents $OCH_3$, $R_2$ and $R_4$ each represent H and $R_3$ represents $CONHCH_3$.

9. A compound according to claim 2 in which $R_1$, $R_2$ and $R_4$ each represent H and $R_3$ represents $CH_3$.

10. A compound according to claim 2 in which $R_1$ represents $OCH_3$, $R_2$ and $R_4$ each represent H and $R_3$ represents $CH_3$.

11. A compound according to claim 2 in which $R_1$ represents $OCH_3$, $R_2$ represents Cl, $R_3$ represents H and $R_4$ represents $CONHCH_3$.

12. A compound according to claim 2 in which $R_1$, $R_2$, $R_3$ and $R_4$ each represent H.

13. A compound according to claim 2 in which $R_1$ represents $OCH_3$, and $R_2$, $R_3$ and $R_4$ each represent H.

14. A compound represented by the general formula

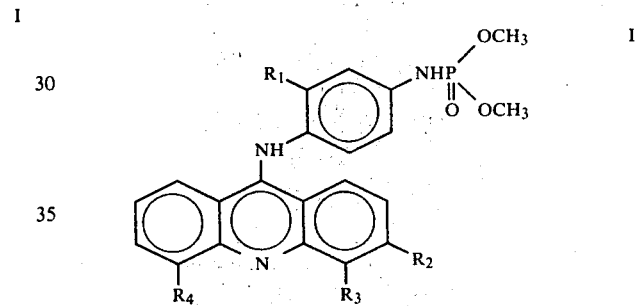

in which $R_1$, $R_3$ and $R_4$ each represent H and $R_2$ represents $NO_2$, or a pharmaceutically acceptable acid addition salt thereof.

15. A compound according to claim 2 in which $R_1$, $R_2$ and $R_4$ each represent H and $R_3$ represents $OCH_3$.

16. A compound according to claim 2 in which $R_1$ and $R_3$ each represent $OCH_3$ and $R_2$ and $R_4$ each represent H.

17. A compound according to claim 2 in which $R_1$, $R_2$ and $R_4$ each represent H and $R_3$ represents $CONHCH_3$.

18. A compound according to claim 2 in which $R_1$ and $R_2$ each represent H and $R_3$ and $R_4$ each represent $CH_3$.

* * * * *